United States Patent [19]

Jelich et al.

[11] Patent Number: 5,103,011
[45] Date of Patent: Apr. 7, 1992

[54] PREPARATION OF 2-CHLORO-5-METHYL-PYRIDINE

[75] Inventors: Klaus Jelich, Wuppertal; Dieter Kaufmann, Bergisch-Gladbach; Bernd Gallenkamp; Reinhard Lantzsch, both of Wuppertal, all of Fed. Rep. of Germany

[73] Assignee: Bayer Aktiengesellschaft, Leverkusen, Fed. Rep. of Germany

[21] Appl. No.: 644,702

[22] Filed: Jan. 23, 1991

[30] Foreign Application Priority Data

Jan. 31, 1990 [DE] Fed. Rep. of Germany ....... 4002729
Jun. 23, 1990 [DE] Fed. Rep. of Germany ....... 4020053

[51] Int. Cl.⁵ .............................. C07D 213/26
[52] U.S. Cl. .................................... 546/345
[58] Field of Search ........................ 546/345

[56] References Cited

U.S. PATENT DOCUMENTS 4,404,388  9/1983  Fäh et al. ..................... 546/345
4,778,896  10/1988 Gallenkamp ................. 546/345
4,897,488  1/1990  Gallenkamp et al. ......... 546/345

OTHER PUBLICATIONS

Chemistry of Heterocyclic Compounds, vol. 14, Supplement, pp. 111–114.

*Primary Examiner*—C. Warren Ivy
*Assistant Examiner*—James H. Turnipseed
*Attorney, Agent, or Firm*—Sprung Horn Kramer & Woods

[57] ABSTRACT

In the preparation of 2-chloro-5-methyl-pyridine of the formula

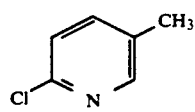

by reacting 3-methyl-pyridine-1-oxide of the formula

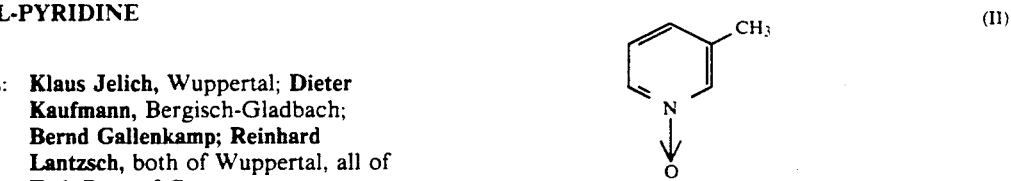

with a chlorinating agent, the improvement which comprises effecting the reaction in the presence of a chlorinating agent of the formula

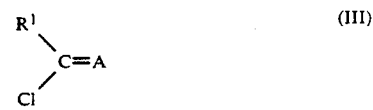

in which
A represents oxygen or the grouping

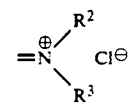

in which
R² and R³ individually represent alkyl, cycloalkyl or aryl or together represent alkanediyl or oxaalkanediyl and
R¹ represents hydrogen, chlorine, alkyl, cycloalkyl, aryl or the grouping

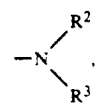

in which R² and
R³ have the abovementioned meanings,
and where, if R¹ represents aryl, A must represent the grouping

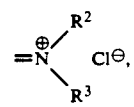

in the presence of a basic organic nitrogen compound and in the presence of a diluent at a temperature between about −20° C. and +120° C. The product is known to be useful in the systhesis of pharmaceuticals and insecticides.

11 Claims, No Drawings

PREPARATION OF 2-CHLORO-5-METHYL-PYRIDINE

The invention relates to a new process for the preparation of 2-chloro-5-methyl-pyridine.

It is known that 2-chloro-5-methyl-pyridine is obtained in addition to 2-chloro-3-methyl-pyridine, 4-chloro-3-methyl-pyridine and 3-chloro-5-methyl-pyridine when 3-methyl-pyridine-1-oxide is reacted with phosphoryl chloride (compare WeiBberger, Chemistry of Heterocyclic Compounds, Pyridine and its Derivatives, Vol. 14, Supplement, Part 2, p. 112). The principal product of this reaction is 4-chloro-3-methyl-pyridine; the proportion of 2-chloro-5-methyl-pyridine is in general below 25%.

It is further known that 2-chloro-5-methyl-pyridine is obtained when 3-methyl-pyridine-1-oxide is reacted with phosphoryl chloride in the presence of a basic organic nitrogen compound and in the presence of a diluent (compare EP-A 324,174). The use of phosphoryl chloride restricts the amount of phosphorus-containing wastes formed, whose disposal is a problem.

A new process for the preparation of 2-chloro-5-methyl-pyridine of the formula (I)

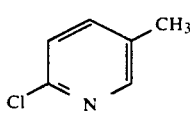

from 3-methyl-pyridine-1-oxide of the formula (II)

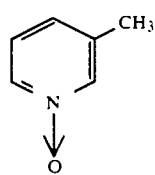

has now been found, which is characterized in that the reaction is carried out in the presence of a chlorinating agent of the general formula (III)

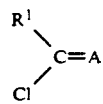

in which
A represents oxygen or the grouping

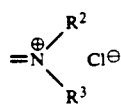

in which
$R^2$ and $R^3$ individually represent alkyl, cycloalkyl or aryl or together represent alkanediyl or oxaalkanediyl and
$R^1$ represents hydrogen, chlorine, alkyl, cycloalkyl, aryl or the grouping

in which $R^2$ and
$R^3$ have the abovementioned meanings,
and where, if $R^1$ represents aryl, A compulsorily represents the grouping

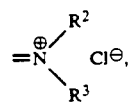

in the presence of a basic organic nitrogen compound and in the presence of a diluent at temperatures between $-20°$ C. and $+120°$ C., and the reaction product is worked up in the customary manner.

It is as surprising that 2-chloro-5-methyl-pyridine can be obtained by the process according to the invention in good yields, as the preparation of this and similar compounds using chlorinating agents of the formula (III) is not known and is also not suggested by previously disclosed processes.

The advantage of the process according to the invention compared to the known prior art is in particular that the chlorinating agent of the formula (III) and its conversion products can be disposed of without relatively large problems.

The process according to the invention thus represents a valuable enrichment of the prior art.

The course of the reaction in the process according to the invention can be outlined, for example, by the following equation:

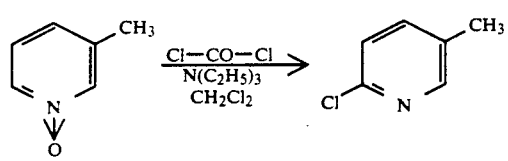

The starting compound of the formula (II) is already known (compare J. Am. Chem. Soc. 76 (1954), 1286–1291).

Formula (III) provides a general definition of the chlorinating agents to be used in the process according to the invention. In the formula (III)
A preferably represents oxygen or the grouping

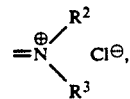

in which $R^2$ and $R^3$ individually represents $C_1$–$C_6$-alkyl, $C_3$–$C_6$-cycloalkyl or phenyl or together represents $C_2$–$C_6$-alkanediyl or $C_2$–$C_5$-oxaalkanediyl and preferably represents hydrogen, chlorine, $C_1$–$C_8$-alkyl, $C_3$–$C_6$-cycloalkyl, phenyl or the grouping

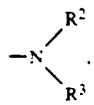

, in which R² and R³ have the meanings indicated above as preferred, and where, if R¹ represents phenyl, A compulsorily represents the grouping

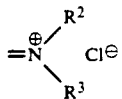

In the formula (III)
A in particular represents oxygen or the grouping

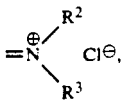

in which R² and R³ individually represent methyl, ethyl, propyl, isopropyl, butyl, isobutyl, cyclopentyl, cyclohexyl or phenyl or together represent butane-1,4-diyl (tetramethylene), pentane-1,5-diyl (pentamethylene) or 3-oxa-pentane-1,5-diyl (—CH₂CH₂—O—Ch₂CH₂—) and R¹ in particular represents hydrogen, chlorine, methyl, ethyl, propyl, isopropyl, butyl, isobutyl, tert.-butyl, 1,1,2-trimethylpropyl, 1,1,3,3-tetramethylbutyl, cyclopentyl, cyclohexyl, phenyl or the grouping

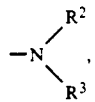

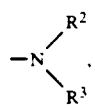

in which R² and R³ have the
meaning indicated above as particularly preferred, and where, if R¹ represents phenyl, A compulsorily represents the grouping

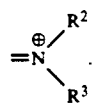

Very particularly preferred chlorinating agents of the formula (III) are those in which A either represents oxygen and R¹ represents chlorine or A represents the grouping

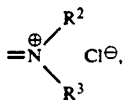

in which R² and R³ represent methyl or ethyl, and R¹ represents chlorine or the grouping

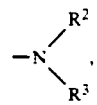

in which R² and R³ represent methyl or ethyl.

The following may be mentioned as examples of the chlorinating agents of the formula (III): phosgene, dichloromethylene-dimethylimmonium chloride and tetramethyl-chloroformamidinium chloride, N,N-dimethyl-N,N'-diethyl-chloroformamidinium chloride and tetraethylchloroformamidinium chloride, pivaloyl chloride, 2,2,3-trimethylbutyryl chloride and 2,2,4,4-tetramethylvaleryl chloride.

The compounds of the formula (III) are known and/or can be prepared by processes which are known per se (compare Angew. Chem. 72 (1960), 836–845; loc. cit 81 (1969), 468; loc. cit. 85 (1973), 837–849; Helv. Chim. Acta 42 (1959) 1653–1671).

The process according to the invention is carried out in the presence of a basic nitrogen compound. Preferred basic organic nitrogen compounds are dialkylamines, such as, for example, diethylamine, dipropylamine, diisopropylamine, dibutylamine, diisobutylamine and dis-ec.-butylamine, trialkylamines, such as, for example, trimethylamine, triethylamine, tripropylamine and tributylamine, methyldiisopropylamine, ethyldiisopropylamine, dialkyl-cycloalkylamines, such as, for example, dimethyl-cyclopentylamine, diethyl-cyclopentylamine, dimethyl-cyclohexylamine and diethyl-cyclohexylamine, dialkyl-aralkylamines, such as, for example, dimethylbenzylamine and diethyl-benzylamine and dialkylarylamines, such as, for example, dimethylaniline.

Particularly preferred basic organic nitrogen compounds are trialkylamines, such as, for example, trimethylamine, triethylamine, tripropylamine, tributylamine, methyldiisopropylamine and ethyldiisopropylamine.

The process according to the invention is carried out in the presence of a diluent. Suitable diluents are virtually all inert organic solvents. These preferably include optionally halogenated hydrocarbons such as pentane, hexane, heptane, octane, cyclohexane, methylcylcohexane, petroleum ether, benzine, ligroin, benzene, toluene, xylene, methylene chloride, chloroform, tetrachloromethane, 1,2-dichloroethane, 1,1,2-trichloroethane, 1,2-dichloropropane, 1,2,3-trichloropropane, chlorobenzene and dichlorobenzene, ethers such as diethyl ether, dipropyl ether, diisopropyl ether, dibutyl ether, methyl tert-butyl ether, methyl tert.-amyl ether, gylcol dimethyl ether, diglycol dimethyl ether, tetrahydrofuran and dioxane, ketones such as acetone, methyl ethyl ketone, diethyl ketone, methyl isopropyl ketone and methyl isobutyl ketone, esters such as methyl acetate, ethyl acetate, propyl acetate, butyl acetate and amyl acetate, nitriles such as acetonitrile and propionitrile, amides such as dimethylformamide, dimethylacetamide and N-methyl-pyrrolidone, and also dimethyl sulphoxide and sulpholane.

The reaction temperatures in the process according to the invention can be varied within a relatively wide range. In general, the reaction is carried out at temperatures between −20° C. and +120° C., preferably at temperatures between −10° C. and +60 ° C.

The process according to the invention is in general carried out under normal pressure. However, it is also possible to work at elevated or reduced pressure of between 0.1 and 10 bar.

In order to carry out the process according to the invention, between 1 and 10 moles, preferably between 1.5 and 4.0 moles, of chlorinating agent of the formula (III) and also between 1 and 10 moles, preferably between 1.5 and 4.0 moles, of the basic organic nitrogen compound are in general employed per mole of 3-methyl-pyridine-1-oxide of the formula (II).

In a preferred embodiment of the process according to the invention, the 3-methyl-pyridine-1-oxide and the basic organic nitrogen compound are initially introduced in a diluent and the chlorinating agent of the formula (III) is then metered in slowly with stirring. The complete reaction mixture is then optionally further stirred until the reaction is complete.

Working-up can be carried out in a customary manner. For example, the reaction mixture is diluted with water and optionally rendered weakly alkaline with sodium hydroxide solution, and the organic phase is separated off. Further product is extracted from the aqueous phase using an organic solvent, such as, for example, methylene chloride. The combined organic phases are dried and filtered; the solvent is carefully removed from the filtrate by distillation in a water jet vacuum.

The residue which remains essentially contains the product of the formula (I), which may be further purified in a customary manner, for example by vacuum distillation.

The 2-chloro-5-methyl-pyridine which can be prepared by the process according to the invention is known as an intermediate for pharmaceuticals (compare DE-A 2,812,585), but can also be employed as an intermediate for insecticides (compare DE-A 2,630,046).

PREPARATION EXAMPLES

EXAMPLE 1

5.6 g (55.3 mmol) of triethylamine are added to 3.0 g (27.5 mmol) of 3-methyl-pyridine-1-oxide in 50 ml of dichloromethane and 9.0 g (55.7 mmol) of dichloromethylene-dimethylimmonium chloride are subsequently added in portions with cooling in an ice bath, the mixture warming to 30° C. The mixture is subsequently stirred at room temperature for one hour, about 50 ml of water are added, the mixture is rendered weakly alkaline using concentration sodium hydroxide solution and the organic phase is separated off. The aqueous phase is extracted using dichloromethane. The combined organic phases are dried, the solvent is stripped off and the residue is analyzed by gas chromatography.

3.2 g of a liquid which has the following composition are obtained: 80% of 2-chloro-5-methyl-pyridine (73% of theory) 20% of 2-chloro-3-methyl-pyridine (18% of theory).

EXAMPLE 2

3.6 g (27.8 mmol) of N-ethyl-diisopropylamine are added to 1.5 g (13.8 mmol) of 3-methyl-pyridine-1-oxide in 30 ml of dichloromethane and 4.7 g (27.7 mmol) of tetramethyl-chloroformamidinium chloride are subsequently added in portions without cooling, the mixture warming to 32° C. The mixture is subsequently stirred for 20 hours, the mixture is poured into water, the phase is separated and the aqueous phase is extracted once more with dichloromethane.

The combined organic phases are dried, the solvent is stripped off and the liquid residue (2.7 g) is analyzed by gas chromatography:
43% of tetramethylurea
10% of 2-chloro-3-methyl-pyridine
44% of 2-chloro-5-methyl-pyridine (68% of theory)

EXAMPLE 3

11.6 g (0.115 mol) of triethylamine are added to 5.0 g (45.9 mmol) of 3-methyl-pyridine-1-oxide in 80 ml of dichloromethane and 11.4 g (0.115 mol) of phosgene are introduced at room temperature.

After the introduction is complete, the mixture is subsequently stirred for a further hour at room temperature, then about 70 ml of water are added and the mixture is rendered alkaline using concentrated sodium hydroxide solution.

The organic phase is separated off, the aqueous phase is subsequently extracted once with dichloromethane and the combined organic phases are dried and concentrated.

4.9 g of a liquid residue which has the composition determined by gas chromatography below are obtained:
64% of 2-chloro-5-methyl-pyridine (54% of theory
11% of 2-chloro-3-methyl-pyridine.

Preparation Example 4

2-Chloro-5-methyl-pyridine 48.2 g (0.4 mol) of trimethylacetyl chloride are added dropwise under nitrogen to a solution of 21.8 g (0.2 mol) of 3-methylpyridine-1-oxide and 40.4 g (0.4 mol) of triethylamine in 200 mol of methylene chloride in the course of 20 minutes. The mixture is subsequently heated under reflux for a further 12 hours, then the precipitate is filtered off with suction, the filter cake is washed with 50 ml of methylene chloride and the solvent is removed by distillation. The bottom is subjected to steam distillation at a ph of 6. The distillate is extracted three times using 100 ml of methylene chloride each time and the extracts are fractionally distilled.

Yield: 15.3 g (60%) of a mixture of 90% of 2-chloro-5-methylpyridine and 10% of 2-chloro-3-methylpyridine.

Pure 2-chloro-5-methyl-pyridine can be separated off by fractional distillation.

Preparation Example 5

2-Chloro-5-methyl-pyridine 59.4 g (0.4 mol) of 2,2,3-trimethylbutyryl chloride are added dropwise under nitrogen to a solution of 21.8 g (0.2 mol) of 3-methylpyridine-1-oxide and 40.4 g (0.4 mol) of triethylamine in 200 ml of methylene chloride in the course of 20 minutes. The mixture is subsequently heated under reflux for a further 12 hours, then the precipitate is filtered off with suction, the filter cake is washed with 50 ml of methylene chloride and the solvent is removed by distillation. The bottom is subjected to steam distillation at a ph of 6. The distillate is extracted three times using 100 ml of methylene chloride each time and the extracts are fractionally distrilled.

Yield: 17.9 g (70%) of a mixture of 93% of 2-chloro-5-methylpyridine and 7% of 2-chloro-3-methylpyridine.

Pure 2-chloro-5-methyl-pyridine can be separated off by fractional distillation.

Preparation Example 6

2-Chloro-5-methyl-pyridine 70.4 g (0.4 mol) of 2,2,4,4-tetramethylvaleryl chloride are added dropwise under nitrogen to a solution of 21.8 g (0.2 mol) of 3-methylpyridine-1-oxide and 40.4 g (0.4 mol) of triethylamine in 200 ml of methylene chloride in the course of 20 minutes. The mixture is subsequently heated under reflux for a further 12 hours, then the precipitate is filtered off with suction, the filter cake is washed with 50 ml of methylene chloride and the solvent is removed by distillation. The bottom is subjected to steam distillation at a pH of 6. The distillate is extracted three times using 100 ml of methylene chloride each time and the extracts are fractionally distilled.

Yield: 17.9 g (70%) of a mixture of 95% of 2-chloro-5-methylpyridine and 5% of 2-chloro-3-methylpyridine.

Pure 2-chloro-5-methyl-pyridine can be separated off by fractional distillation.

It is understood that the specification and examples are illustrative but not limitative of the present invention and that other embodiments within the spirit and scope of the invention will suggest themselves to those skilled in the art.

We claim:

1. In the preparation of 2-chloro-5-methyl-pyridine of the formula

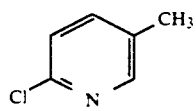

(I)

by reacting 3-methyl-pyridine-1-oxide of the formula

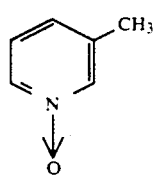

(II)

with a chlorinating agent, the improvement which comprises effecting the reaction in the presence of a chlorinating agent of the formula

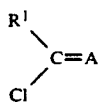

(III)

in which
A represents oxygen or the grouping

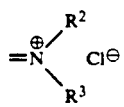

in which
$R^2$ and $R^3$ individually represent alkyl, cycloalkyl or aryl or together represent alkanediyl or oxaalkanediyl and
$R^1$ represents hydrogen, chlorine, alkyl, cycloalkyl, aryl or the grouping

in which $R^2$ and
$R^3$ have the abovementioned meanings, and where, if $R^1$ represents aryl, A must represent the grouping

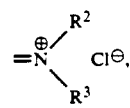

in the presence of a basic organic nitrogen compound and in the presence of a diluent at a temperature between about $-20°$ C. and $+120°$ C.

2. A process according to claim 1, in which
$R^2$ and $R^3$ individually represent $C_1$-$C_8$-alkyl, $C_3$-$C_6$-cycloalkyl or phenyl or together represent $C_2$-$C_6$-alkanediyl or $C_2$-$C_5$-oxaalkanediyl and
$R^1$ represents hydrogen, chlorine, $C_1$-$C_8$-alkyl, $C_3$-$C_6$-cycloalkyl, phenyl or the grouping

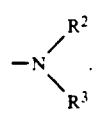

3. A process according to claim 1, in which
$R^2$ and $R^3$ individually represent methyl, ethyl, propyl, isopropyl, butyl, isobutyl, cyclopentyl, cyclohexyl or phenyl or together represent butane-1,4-diyl (tetramethylene), pentane-1,5-diyl (pentamethylene) or 3-oxapentane-1,5-diyl ($-CH_2CH_2-O-CH_2CH_2-$) and
$R^1$ represents hydrogen, chlorine, methyl, ethyl, propyl, isopropyl, butyl, tert.-butyl, 1,1,2-trimethylpropyl, 1,1,3,3-tetramethylbutyl, isobutyl, cyclopentyl, cyclohexyl, phenyl or the grouping

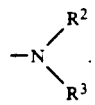

4. A process according to claim 1, in which
A either represents oxygen and $R^1$ represents chlorine or A represents the grouping

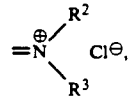

in which $R^2$ and $R^3$ represent methyl or ethyl, and $R^1$ represents chlorine or the grouping

in which $R^2$ and $R^3$ represent methyl or ethyl.

5. A process according to claim 1, wherein the chlorinating agent is selected from the group consisting of phosgene, dichloromethylene-dimethylimmonium chloride and tetramethyl-chloroformamidinium chloride, N,N-dimethyl-N', N'-diethyl-chloroformamidinium chloride and tetraethyl-chloroformamidinium chloride, pivaloyl chloride, 2,2,3-trimethylbutyryl chloride and 2,2,4,4-tetramethylvaleryl chloride.

6. A process according to claim 1, wherein the basic organic nitrogen compound is selected from the group consisting of a dialkylamine, trialkylamine, dialkyl-cycloalkylamine, dialkyl-aralkylamine and dialkylarylamine.

7. A process according to claim 1, wherein the basic organic nitrogen compound is selected from the group consisting of diethylamine, dipropylamine, diisopropylamine, dibutylamine, diisobutylamine, di-sec.-butylamine, trimethylamine, triethylamine, tripropylamine, tribtylamine, methyldiisopropylamine, ethyldiisopropylamine, dimethyl-cyclopentylamine, diethyl-cyclopentylamine, dimethyl-cyclohexylamine, dimethyl-benzylamine, diethyl-benzylamine and dimethylaniline.

8. A process according to claim 1, wherein the reaction is carried out in the presence of an inert organic solvent as diluent.

9. A process according to claim 1, wherein the reaction is carried out at a temperature between about $-10°$ C. and $+60°$ C.

10. A process according to claim 1, wherein about 1 to 10 moles of the chlorinating agent and between about 1 to 10 moles of the basic organic nitrogen compound are employed per mole of 3-methyl-pyridine-1-oxide.

11. A process according to claim 1, wherein the 3-methyl-pyridine-1-oxide and the basic nitrogen compound are initially introduced in a diluent and the chlorinating agent is slowly metered in.

* * * * *

UNITED STATES PATENT AND TRADEMARK OFFICE
CERTIFICATE OF CORRECTION

PATENT NO. : 5,103,011

DATED : April 7, 1992

INVENTOR(S) : Jelich et al.

It is certified that error appears in the above-identified patent and that said Letters Patent is hereby corrected as shown below:

Col. 9, last line   Delete " tribtylamine " and substitute
— tributylamine —

Signed and Sealed this

Second Day of November, 1993

Attest:

BRUCE LEHMAN

Attesting Officer   Commissioner of Patents and Trademarks